United States Patent [19]
Graber et al.

[11] Patent Number: 5,370,647
[45] Date of Patent: Dec. 6, 1994

[54] TISSUE AND ORGAN EXTRACTOR

[75] Inventors: John N. Graber, Mpls; Michael T. Hofflander, Edina; Mark A. Schmidt, Hutchinson, all of Minn.

[73] Assignee: Surgical Innovations, Inc., Minneapolis, Minn.

[21] Appl. No.: 61,629

[22] Filed: May 13, 1993

Related U.S. Application Data

[63] Continuation-in-part of Ser. No. 848,747, Mar. 10, 1992, abandoned, which is a continuation-in-part of Ser. No. 644,987, Jan. 23, 1991, Pat. No. 5,190,561.

[51] Int. Cl.$^5$ .............................................. A61B 17/22
[52] U.S. Cl. ..................................................... 606/127
[58] Field of Search .............. 128/749, 751; 606/114, 606/127

[56] References Cited

U.S. PATENT DOCUMENTS

| | | | |
|---|---|---|---|
| 4,347,846 | 9/1982 | Dormia | 606/127 |
| 4,997,435 | 3/1991 | Demeter | 606/127 |
| 5,074,867 | 12/1991 | Wilk | 606/127 |
| 5,147,371 | 9/1992 | Washington et al. | 606/127 |
| 5,176,687 | 1/1993 | Hasson et al. | 606/127 |
| 5,190,542 | 3/1993 | Nakao et al. | 606/114 |
| 5,190,555 | 3/1993 | Wetter et al. | 606/127 |
| 5,192,284 | 3/1993 | Pleatman | 606/127 |
| 5,192,286 | 3/1993 | Phan et al. | 606/127 |
| 5,234,439 | 8/1993 | Wilk et al. | 606/127 |

FOREIGN PATENT DOCUMENTS 0003301 8/1979 United Kingdom .............. 606/127

*Primary Examiner*—Max Hindenburg
*Attorney, Agent, or Firm*—Dorsey & Whitney

[57] ABSTRACT

A tissue and organ extractor is provided for use during laparoscopic surgical procedures. The tissue and organ extractor has a handle, an elongated shank, and a flexible collapsible working end. The handle includes lock for locking a grasping instrument, such as forceps, securely in place in relation to the tissue and organ extractor. The extractor is inserted through a cannula into an abdominal cavity and the tissue or organ to be removed is manipulated into the working end by a grasping instrument. The extractor, grasping instrument and tissue are removed from the abdominal cavity through the cannula. The working end envelops the tissue and, during removal, compresses the enveloped tissue.

27 Claims, 9 Drawing Sheets

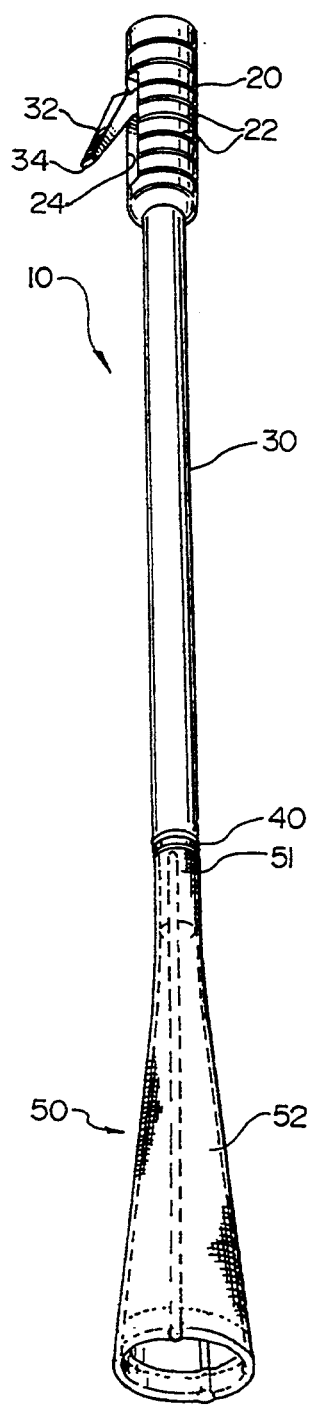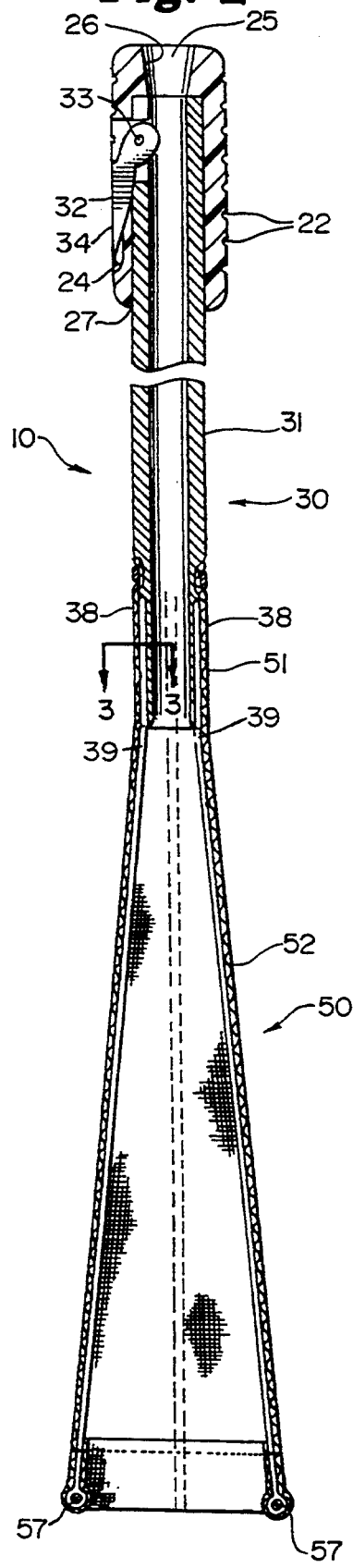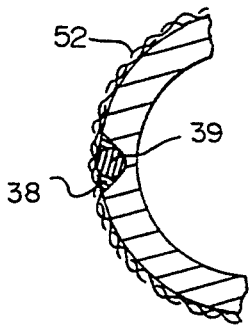

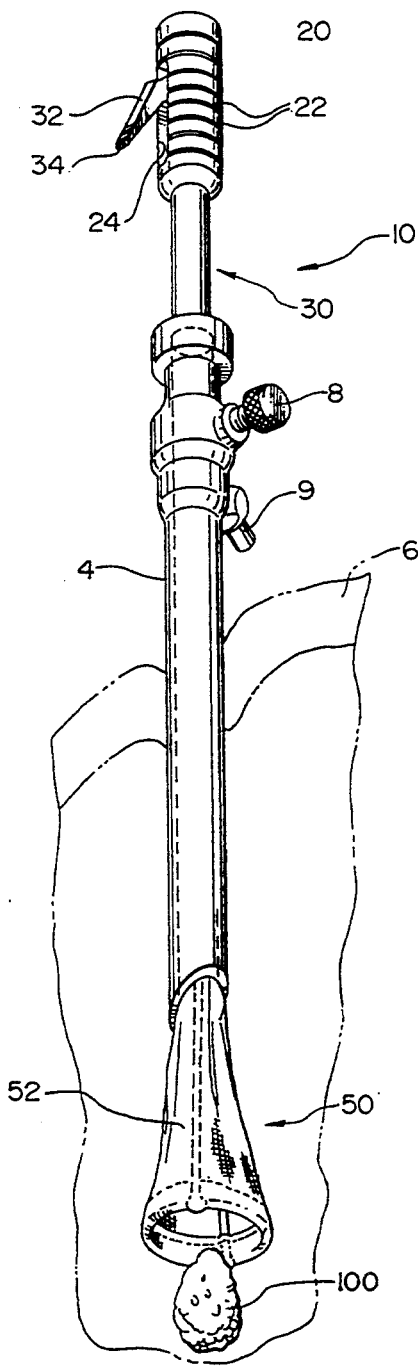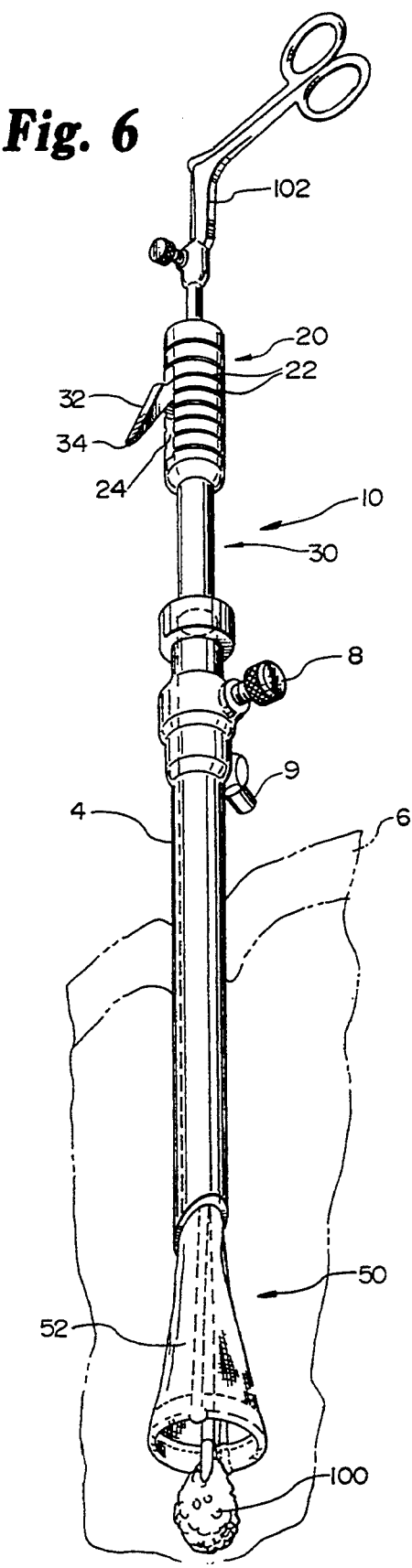

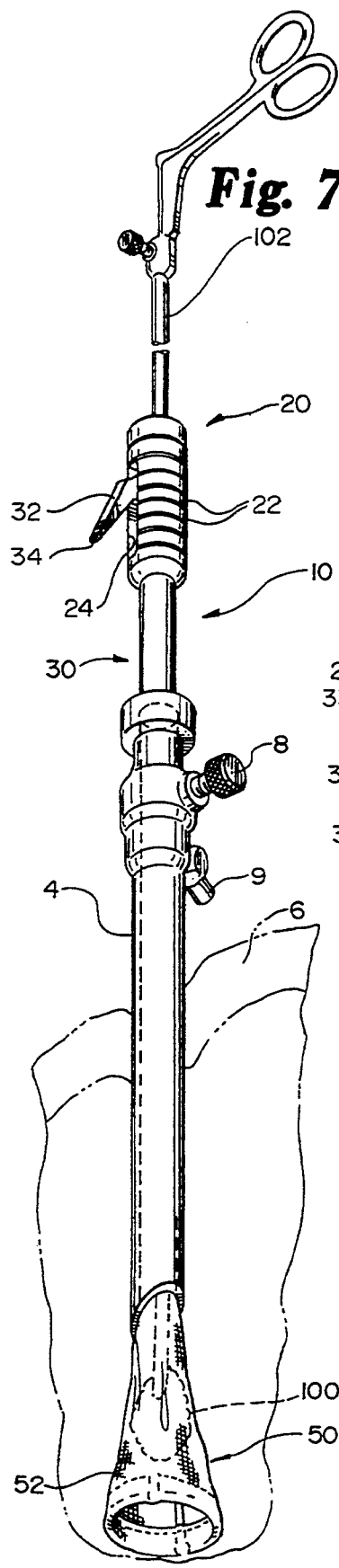
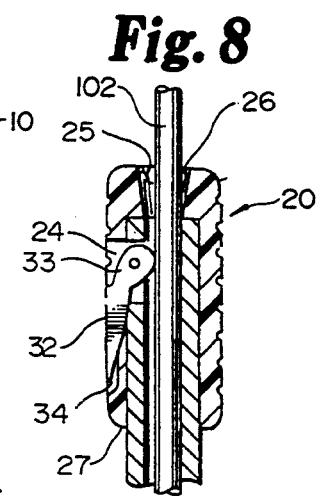
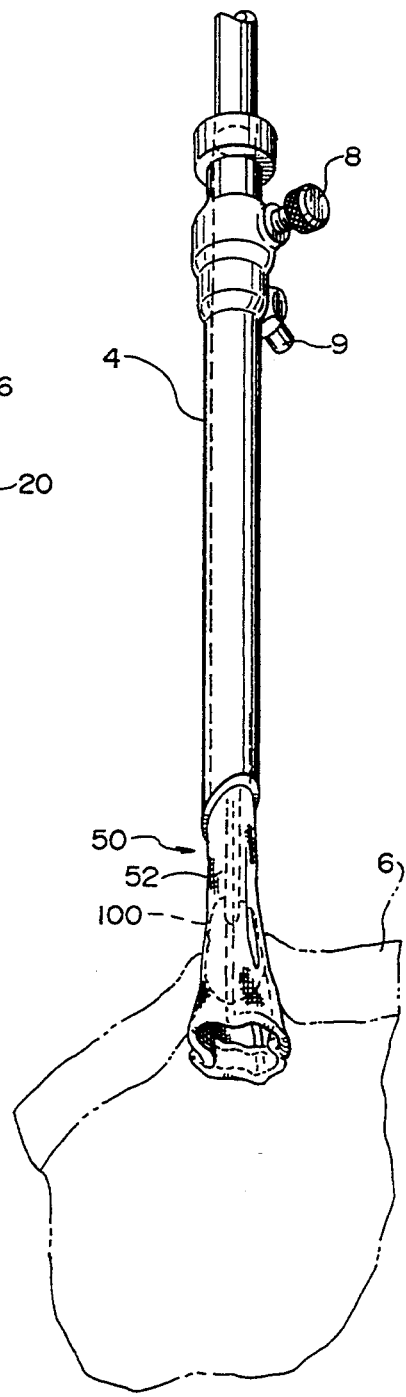

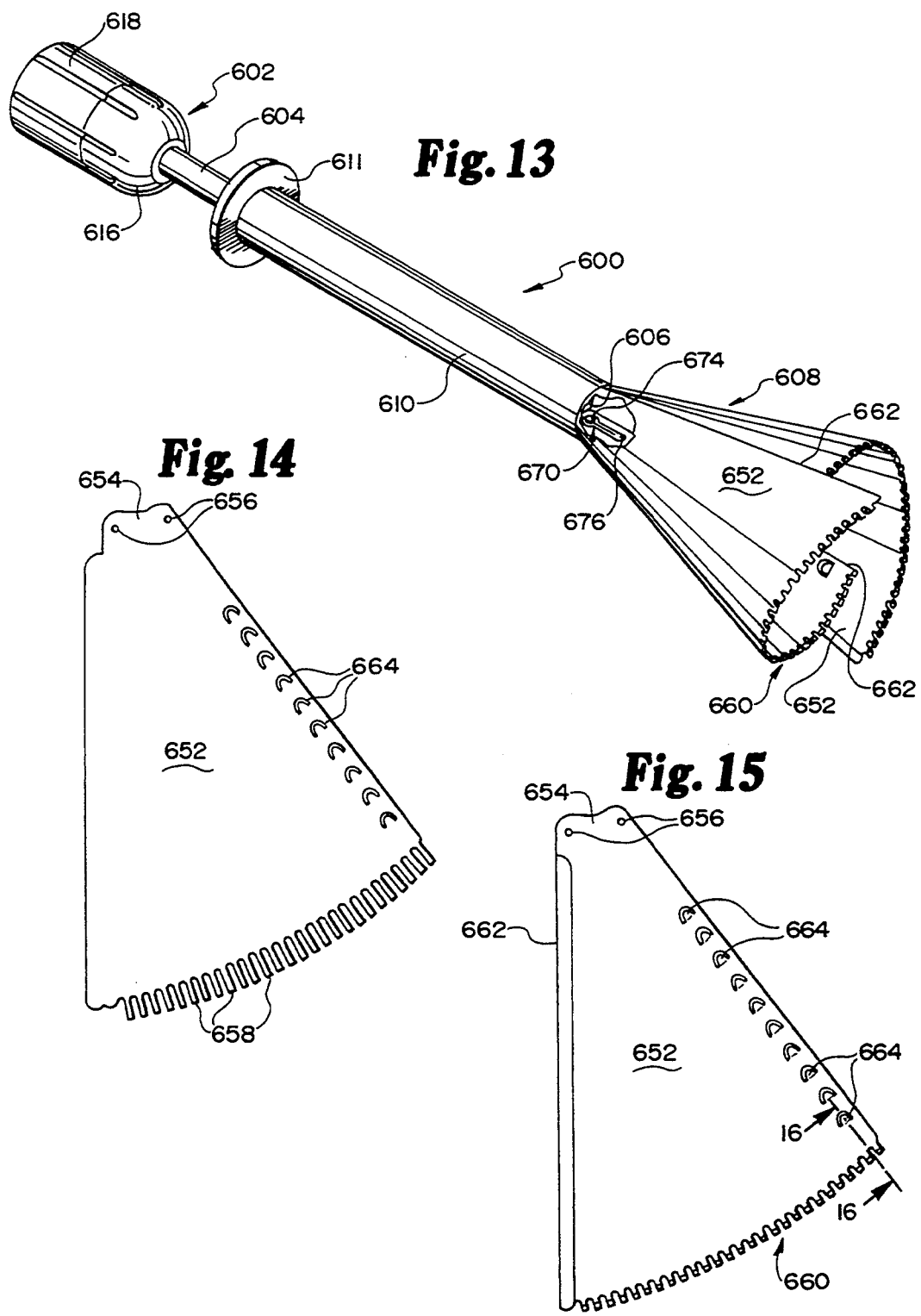

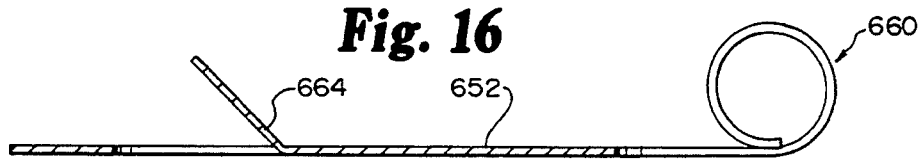
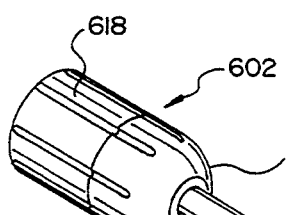
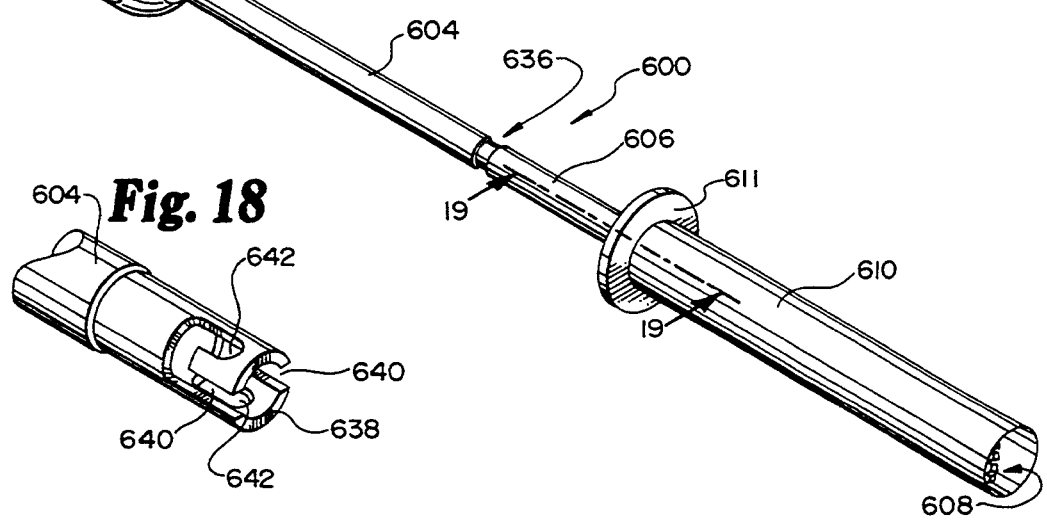
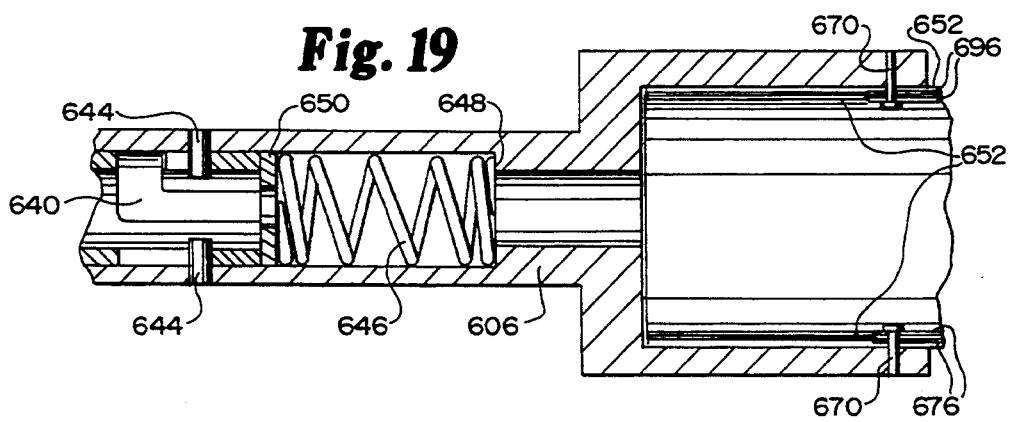

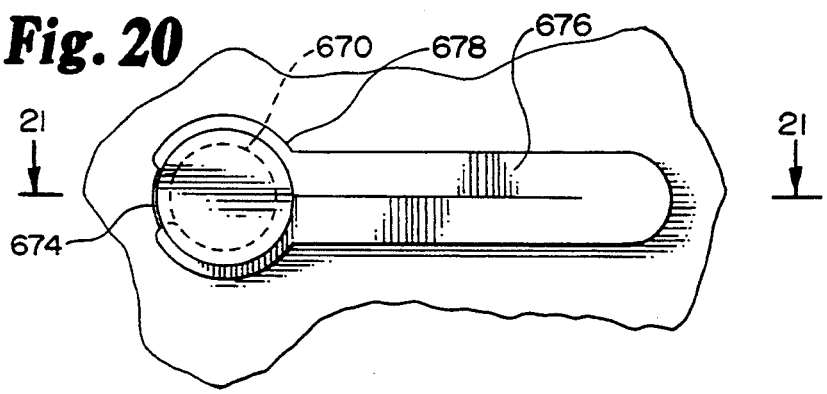
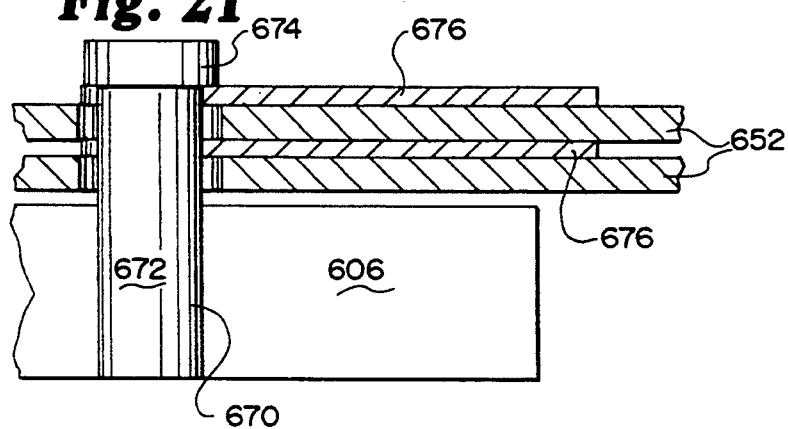
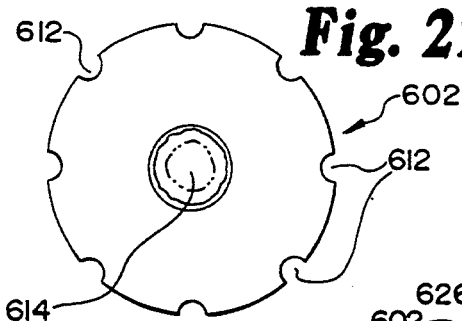
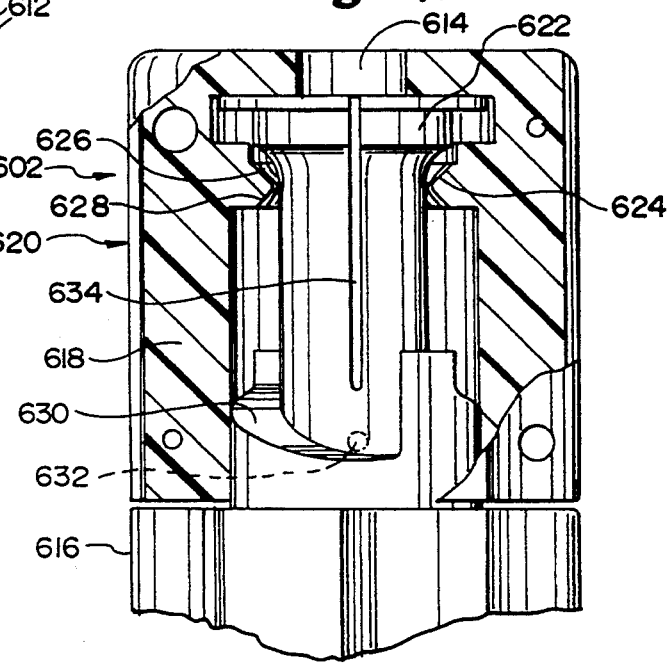

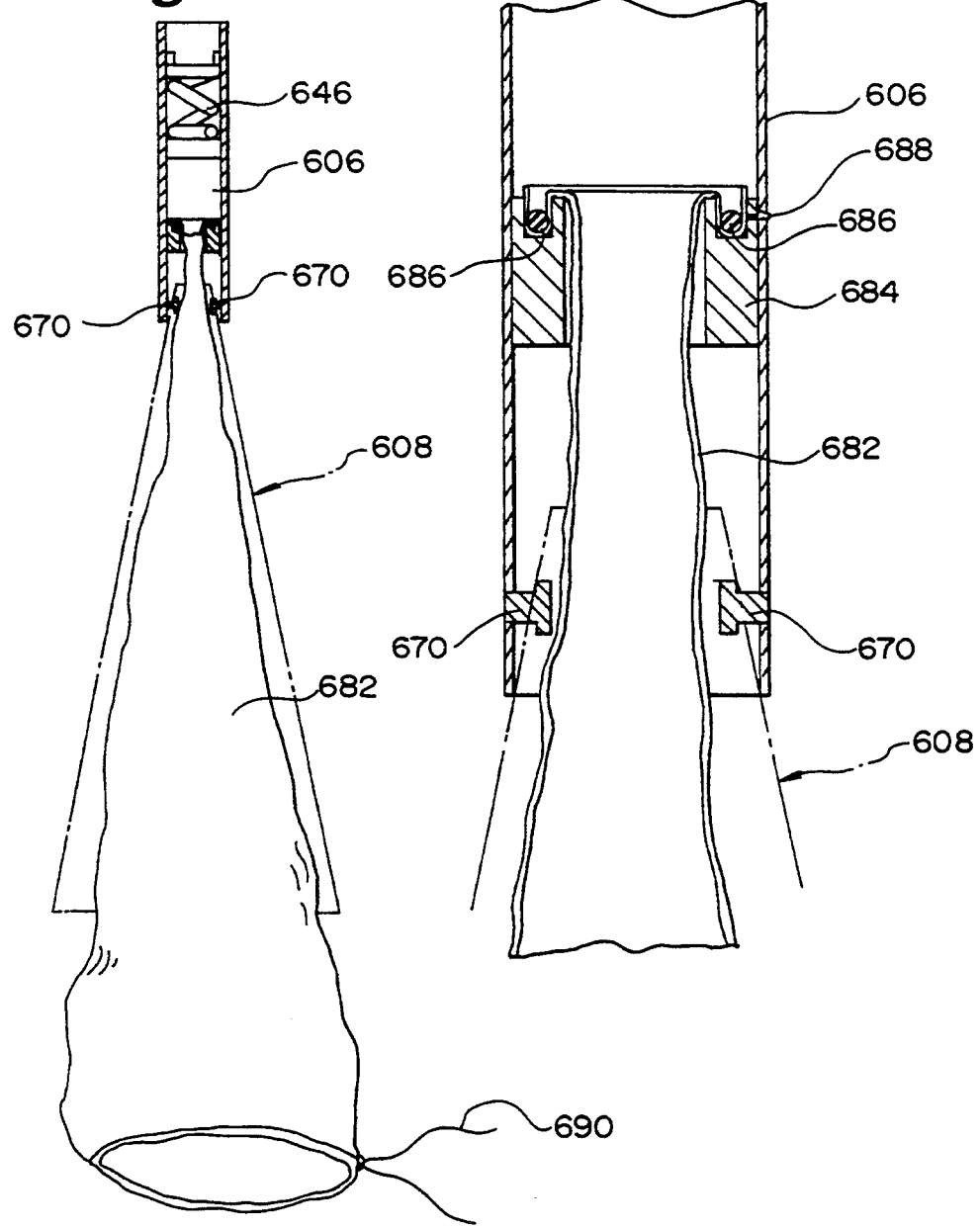

TISSUE AND ORGAN EXTRACTOR

This application is a continuation-in-part of co-pending application Ser. No. 07/848,747, filed Mar. 10, 1992, now abandoned in turn a continuation-in-part of application Ser. No. 07/644,987, filed Jan. 23, 1991, now U.S. Pat. 5,190,561.

Background of the Invention

This invention relates generally to the field of surgical instruments. In particular, this invention relates to a surgical instrument for use in laparoscopy wherein the instrument may be used to envelop an organ or tissue to facilitate its removal from a patient through a small puncture orifice.

Laparoscopy is a form of surgery that involves visualizing the interior of the abdominal cavity using an illuminating optical instrument, a laparoscope. The laparoscope and other instruments are introduced into the abdominal cavity through small puncture orifices in the abdominal wall.

Laparoscopic procedures are commenced by using a device known as a trocar. The trocar comprises a cannula or trocar sleeve (a hollow sheath or sleeve with a central lumen) and an obturator. The obturator is a solid metal rod with an extremely sharp three-cornered tip that is received in the cannula. The trocar is used to penetrate the abdominal wall. The obturator is withdrawn from the cannula after the intra-abdominal end of the trocar is in the abdominal cavity. The cannula remains in the abdominal wall throughout the surgical procedure. This allows surgical instruments used during laparoscopic procedures to be introduced in the abdominal cavity through the cannula. Trocars are available in different sizes to accommodate various instruments.

Laparoscopy traditionally has been used almost exclusively for gynecological surgery. However, physicians specializing in other fields have begun to recognize the diagnostic and operative value of laparoscopy.

The advantages of laparoscopic surgery include: procedures may be performed on an outpatient basis; surgeons are given the opportunity to view intra-abdominal viscera without performing a laparotomy, a large incision of the abdominal wall; small puncture wounds are created rather than large incisions, lessening trauma; incision sites for laparotomies may be determined; patient and insurer medical costs are reduced by shorter hospital stays; and postoperative patient discomfort, with recovery times measured in days as opposed to weeks, is lessened.

Thus, there is a substantial interest in and need for providing task specific surgical instruments particularly adapted to general surgical procedures now being performed laparoscopically. Because laparoscopy is an evolving specialty within the field of general surgery, currently available instruments inadequately meet the needs of laparoscopic surgeons.

One of the problems associated with existing instruments used in laparoscopy is that when soft tissue or organs are removed through the cannula, the tissue or organ being removed can tear. If parts of the tissue or organ to be removed during the procedure are left in the abdominal cavity, infection may result. In order to avoid this result, the surgeon would have to create a relatively large incision in the abdominal wall to remove the tissue or organ. However, such a procedure would defeat the purpose and benefit of performing laparoscopic surgery.

It would, therefore, be desirable to provide a tissue and organ extractor that can be used to extract tissue and organs safely and completely from the abdominal cavity of a patient without tearing the tissue and organs.

It would also be desirable to provide a tissue and organ extractor that can be used during laparoscopic surgery.

SUMMARY OF THE INVENTION

It is an object of this invention to provide a tissue and organ extractor that can be used to extract tissue or organs safely and completely from the abdominal cavity of a patient without tearing the tissue or organs.

It is another object of this invention to provide a tissue and organ extractor that can be used during laparoscopic surgery for extracting tissue, organs or the like, and for implanting or inserting prostheses.

Yet another object of the present invention is to provide a partially disposable tissue organ extractor for use in laparoscopic surgical procedures wherein the extractor includes a reusable handle portion.

In accordance with this invention there is provided a tissue and organ extractor for use during laparoscopic surgery having a handle, with a central bore, connected to one end of a hollow shank. The other end of the shank is adapted to be connected releasably to one end of tubular plunger rod. A flexible self-deploying enveloping means with a free open end is connected to the other end of the plunger rod. A tubular extractor introducing shroud is coaxially and concentrically positioned about the enveloping means. When aligned and connected together, the handle, shank, rod, enveloping means and shroud define a central passageway through the tissue and organ extractor. This passageway allows an instrument such as a forceps or clamp to be inserted through the tissue or organ extractor and extend past the open end of the enveloping means. The instrument thus inserted can be used to grasp the tissue or organ for removal from the abdominal cavity. The handle of the extractor includes a lock for locking the forceps in place relative to the extractor.

In use, the enveloping means is contained in the shroud, with the end of the rod extending therefrom for connection to the shank. The assembled tissue extractor is inserted through a cannula into a patient's abdomen. The enveloping means is deployed by pushing it from the shroud, whereupon it expands into its fully deployed cone shape with a large open end, the smaller end of the cone-shaped enveloping means being connected to the rod and having an inner diameter approximately equal to the inner diameter of the rod. The enveloping means is moved close to the organ or tissue to be removed. The surgeon inserts a forceps through the hollow passageway running the length of the extractor, past the open end of the enveloping means to grasp the tissue or organ to be removed. The tissue or organ is then drawn inside the enveloping means. The surgeon may lock the forceps in place relative to the tissue and organ extractor. The enveloping means is withdrawn into the shroud by pulling outwardly, causing the enveloping means to collapse around the tissue and return to its pre-deployment, multilayer generally cylindrical tubular configuration inside the shroud, compressing the tissue therein. The extractor may then be drawn out of the cannula, or the forceps, the tissue and organ extractor containing the tissue and the cannula, if desired, can all be removed from the patient's abdomen through the small puncture orifice originally created by the trocar.

An advantage of the extractor of the present invention is that it prevents the traumatic manipulation of the organ or tissue as it passes into the cannula or through the puncture orifice, allowing the organ or tissue to be removed safely and completely from the abdominal cavity.

BRIEF DESCRIPTION OF THE DRAWINGS

The above and other objects and advantages of this invention will be apparent upon consideration of the following detailed description, in conjunction with the accompanying drawings.

FIG. 1 is a perspective view of one embodiment of the tissue and organ extractor of this invention;

FIG. 2 is a longitudinal cross sectional view of one embodiment of the tissue and organ extractor of this invention;

FIG. 3 is a fragmentary sectional view taken along line 3—3 of FIG. 2;

FIG. 5 is a perspective view of one embodiment of the tissue and organ extractor of this invention fully inserted into the abdomen through a cannula;

FIG. 6 is a perspective view of one embodiment of the tissue and organ extractor of this invention fully inserted into the abdomen through a cannula with tissue to be extracted from the abdomen held by the grasper jaws of a forceps;

FIG. 7 is a view similar to the view of FIG. 6 but with the tissue drawn up inside the enveloping means of the tissue and organ extractor by the forceps;

FIG. 8 is a partial sectional view showing the locking lever of the handle engaged with the shaft of the forceps;

FIG. 9 is a fragmentary perspective view of one embodiment of the tissue and organ extractor of this invention showing the enveloping means, forceps and tissue being extracted through the puncture orifice in the abdominal wall;

FIG. 13 is a perspective view of a third embodiment of the tissue and organ extractor of the present invention depicting the generally cone-shaped tissue enveloping means thereof fully deployed;

FIG. 14 is a plan view of one of the leaves of the enveloping means prior to being connected to the extractor of the third embodiment;

FIG. 15 is a plan view of the leaf depicted in FIG. 14, with portions of the leaf having been manipulated prior to connecting it to the extractor of the third embodiment;

FIG. 16 is a sectional view taken along line 16—16 in FIG. 15;

FIG. 17 is a perspective view of the third embodiment depicting it in its predeployment configuration and ready for insertion into a patient's abdomen;

FIG. 18 is a fragmentary perspective view of part of the joint between the shank and rod of the third embodiment;

FIG. 19 is a sectional view taken along line 19—19 in FIG. 17;

FIG. 20 is a fragmentary view of part of the connection between the leaves and the rod of the third embodiment;

FIG. 21 is a sectional view taken along line 21—21 in FIG. 20;

FIG. 22 is a elevational view of the handle end of the third embodiment of the extractor of the present invention;

FIG. 23 is a fragmentary view of the handle, with portions broken away for clarity, depicting the lock of the third embodiment of the present invention;

FIG. 24 is a simplified mechanical diagram of the third embodiment of the present invention with a containment web membrane attached thereto; and FIG. 25 is a fragmentary sectional view depicting the connection between the containment web member depicted in FIG. 24 and the plunger rod of the third embodiment of the present invention.

DETAILED DESCRIPTION OF THE INVENTION

Figure 4:
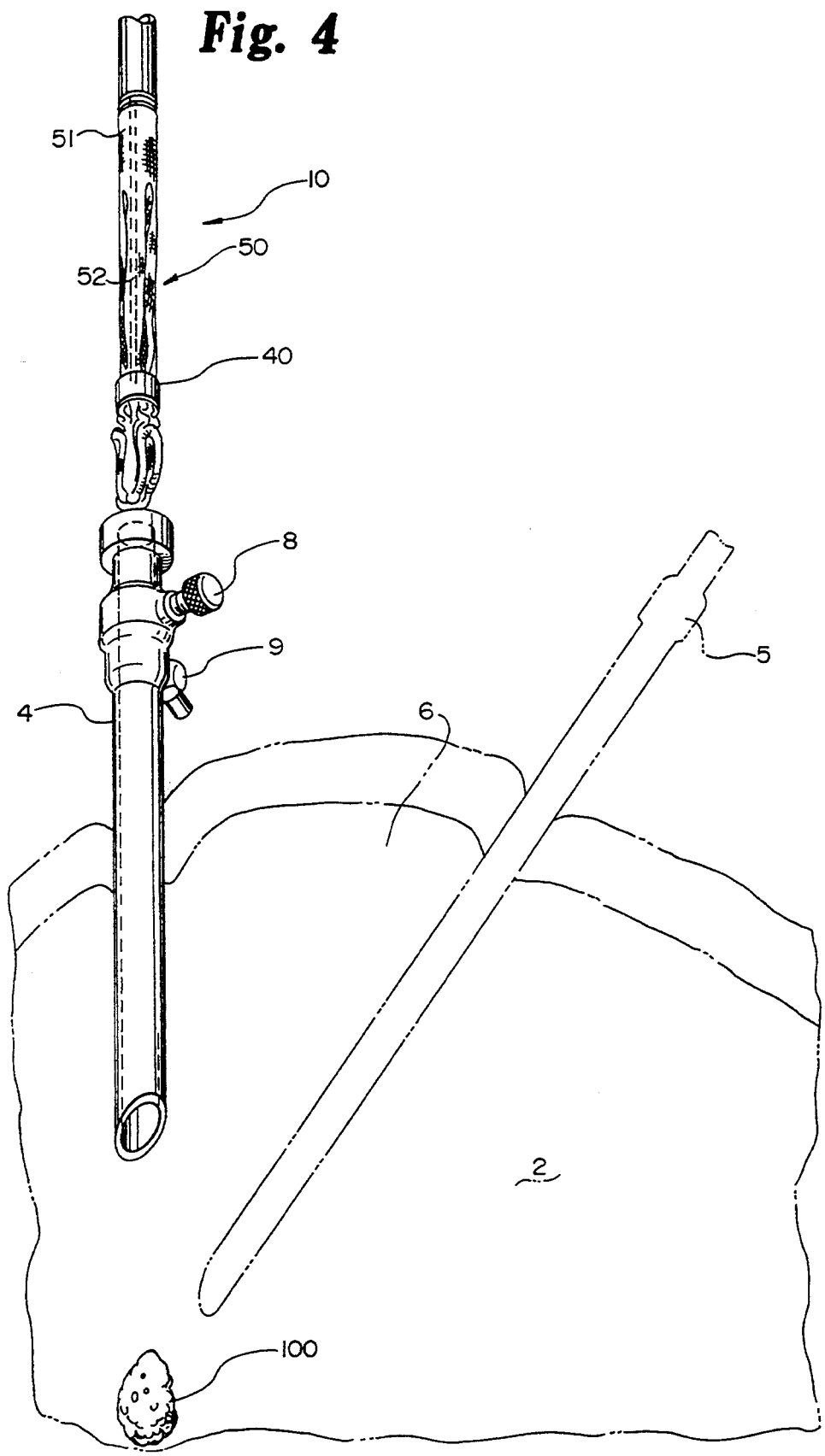
FIG. 4 is a fragmentary perspective view of one embodiment of the tissue and organ extractor of this invention positioned for insertion into a cannula, with phantom lines depicting the intra-abdominal region of a patient and an auxiliary laparoscopic device.

One embodiment of the tissue and organ extractor of the present invention is shown in FIGS. 1-9. The tissue and organ extractor 10 includes a hollow handle 20, an elongated, generally central shank 30, a ring 40 and an enveloping means 50.

The handle 20 includes an upper end, a lower end, circumferentially cut grooves 22, a recess 24 and a hollow chamber 25. The grooves 22 are designed to permit the surgeon to grasp and manipulate the tissue and organ extractor 10 more easily. The handle 20 has an outer diameter larger than the outer diameter of the shank 30. This prevents the tissue and organ extractor 10 from falling completely through the cannula 4 inserted through the abdominal wall 6. Preferably, the handle 20 is made from an elastomeric synthetic resin or some other suitable hand graspable material.

The hollow chamber 25 includes a top portion 26 and a lower portion 27. The diameter of the lower portion 27 of the hollow chamber 25 is about the same as the outer diameter of the shank 30. This allows one end of the shank 30 to be received within the lower portion 27 of the handle 20. The hollow portion 31 of the shank 30 is thus in communication with the top portion 26 of the hollow chamber 25 of the handle 20. This allows a surgical instrument such as a forceps to be inserted through the handle 20 and shank 30 and into the enveloping means 50. Preferably, the top portion 26 of the hollow chamber 25 is flared outwardly toward the upper end of the handle 20. This facilitates the insertion of an instrument into the hollow chamber 25 of the handle 20.

A locking lever 32 is pivotally connected to the shank 30 adjacent the distal end thereof. The locking lever 32 includes a cam like head 33 and a finger-tip grasping end 34. The locking lever 32 pivots to allow the head 33 to extend into the hollow portion 31 and engage the shaft of an instrument inserted through the hollow portion 31 of the shank 30. The locking lever 32 is received in the recess 24 and is generally shorter than the recess 24 to permit the surgeon to easily grasp the finger-tip grasping end 34.

A plurality of longitudinally cut grooves 38 are formed at one end of the shank 30. The grooves 38 are preferably equally spaced from one another about the circumference of the shank 30. A plurality of flexible wires 39 extend from one end of the shank 30 to the open end of the enveloping means 50. One of these wires 39 is received in each of the grooves 38 formed at one end of the shank 30.

The enveloping means 50 includes a neck 51 that is attached to the proximal end of the shank 30 and a flexible web 52 for enveloping the tissue or organ to be removed from a patient. Preferably, the inner diameter of the neck 51 is about the same as the outer diameter of the shank 30. This facilitates the attachment of the neck 51 to the proximal end of the shank 30 and also facilitates the travel of an instrument through the shank 30 to the enveloping means 50. The enveloping means 50 flares outwardly from the neck 51. The amount of this outward flare may be varied depending on the diameter of the tissue or organ to be removed from the abdominal cavity 2.

The web 52 preferably is attached to a portion of the shank 30 so that the web 52 covers the wires 39 extending along the grooves 38. The web 52 may be attached to the outside of the wires 39 by threading, heat pressing or other suitable means. The web 52 thus holds the wires 39 flush against the grooves 38 in the shank 30. Of course, the wires 39 could also be held flush against the grooves 38 by soldering, plastic adhesive, resin or some other suitable adhesive means. The wires 39 are biased outwardly to ensure that the web 52 is flared outwardly.

The web 52 is preferably made from a sturdy waterproof, stain resistant fabric such as treated sail cloth or duck cloth. One end of the web 52 is connected to one end of the shank 30 by screws, snaps or other suitable fastening means. The other end of the web 52 is folded over and joined to itself by threading, heat pressing, plastic adhesive or other suitable fastening means.

A cable 57 is located inside the folded portion of the web 52 adjacent to the apex of the folded over portion of the web 52. The cable 57 is received through the eye ends of the outwardly biased wires 39. The cable 57 should be long enough so that the open end of the enveloping means 50 can open sufficiently wide to allow access thereto by tissue or organs to be removed from the patient.

The ring 40 is slidably positioned over the neck 51 when the enveloping means 50 is in its outwardly flared position. Prior to the insertion of the tissue and organ extractor 10 into the cannula 4, the ring 40 is slid down from the neck 51 toward the open end of the enveloping means 50. This collapses the enveloping means 50 to facilitate the insertion of the tissue and organ extractor 10 into the cannula 4. After the open end of the enveloping means 50 has entered the cannula 4, the ring 40 engages the top of the cannula 4. This prevents the ring 40 from traveling any further through the cannula 4. Once the ring 40 engages the top of the cannula 4, the tissue and organ extractor 10 can still travel through the cannula 4 a distance equal to the distance that the ring 40 can travel along the length of the web 52. This distance should be sufficiently long so that the enveloping means 50 can emerge from the end of the cannula 4 and flare outwardly to present an open area for insertion of tissue or organs into the enveloping means 50.

The inner diameter of the ring 40 is preferably about the same as the outer diameter of the neck 51. The outer diameter of the ring 40 is preferably larger than the inner diameter of the cannula 4. This precludes the ring 40 from entering the cannula 4 when the tissue and organ extractor 10 is inserted therein. Of course, a shoulder means could be used inside the cannula 4 and a small ring 40 could be used to achieve the same result.

The operation of the tissue and organ extractor 10 will now be described. Referring to FIG. 4, an auxiliary cannula 5 is introduced into the abdominal cavity 2. A laparoscope (not shown) is introduced into the abdominal cavity 2 through the cannula 5. The laparoscope, which is an illuminating optical instrument, is used to visualize the interior of the abdominal cavity 2. A camera (not shown) is placed over the eyepiece of the laparoscope and the laparoscopic procedure is monitored on a television screen. The cannula 4 is introduced into the abdominal cavity 2 to provide the passageway for the laparoscopic instruments necessary to perform any particular laparoscopic surgical procedure, including any procedure in which the present invention may be utilized.

Prior to the insertion of the tissue and organ extractor 10 into the cannula 4, the enveloping means 50 is collapsed as shown in FIG. 4 by lowering the ring 40 over the web 52. The tissue and organ extractor 10 is then introduced through the cannula 4 into the abdominal cavity 2.

The open end of the web 52 is placed in dose proximity to the tissue or organ 100 to be removed from the abdominal cavity 2. Once the open end of the web 52 is properly positioned, the tissue and organ extractor 10 is locked into place by set screws 8 and 9 located on the cannula 4. A forceps 102 is introduced into the abdominal cavity 2 through the hollow portion of the tissue and organ extractor 10. The surgeon manipulates the forceps 102 to grasp the tissue or organ 100 and draw it into the open end of the web 52.

Using the locking lever 32, the surgeon locks the forceps 102 in place in relation to the tissue and organ extractor 10. The tissue or organ 100 is thus held in place inside the web 52. The surgeon then removes the cannula 4, tissue and organ extractor 10, forceps 102 and tissue or organ 100 simultaneously through the small puncture orifice in the abdominal wall through which the cannula 4 was originally inserted. As all of these items are being removed through the small puncture orifice, the web 52 collapses from its outwardly flared configuration, to a collapsed configuration thereby compressing and enveloping the tissue or organ 100. The open end of web 52 constricts as it passes through the small puncture orifice and forms a seal preventing the tissue or organ 100 or parts that may break off from reentering the abdominal cavity 2.

Figure 10:
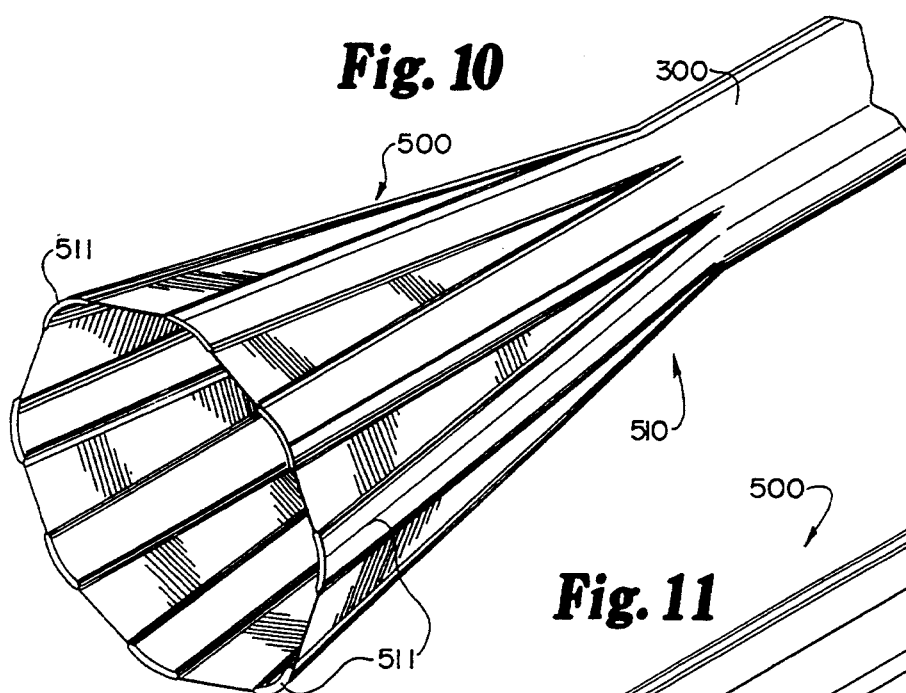
FIG. 10 is a fragmentary perspective view of a portion of the enveloping means of a second embodiment of the tissue and organ extractor of this invention showing the enveloping means in its normal outwardly biased position.
Figure 11:
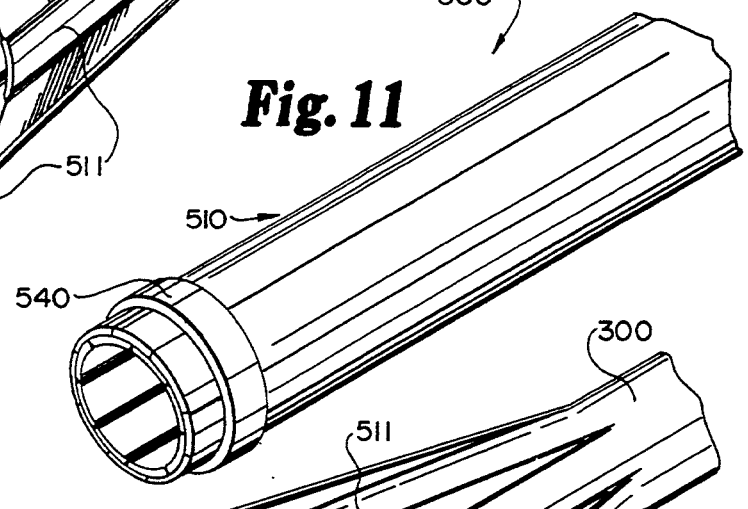
FIG. 11 is a fragmentary perspective view of a portion of the enveloping means of a second embodiment of the tissue and organ extractor of this invention showing the enveloping means in a closed position for insertion and travel through the cannula.
Figure 12:
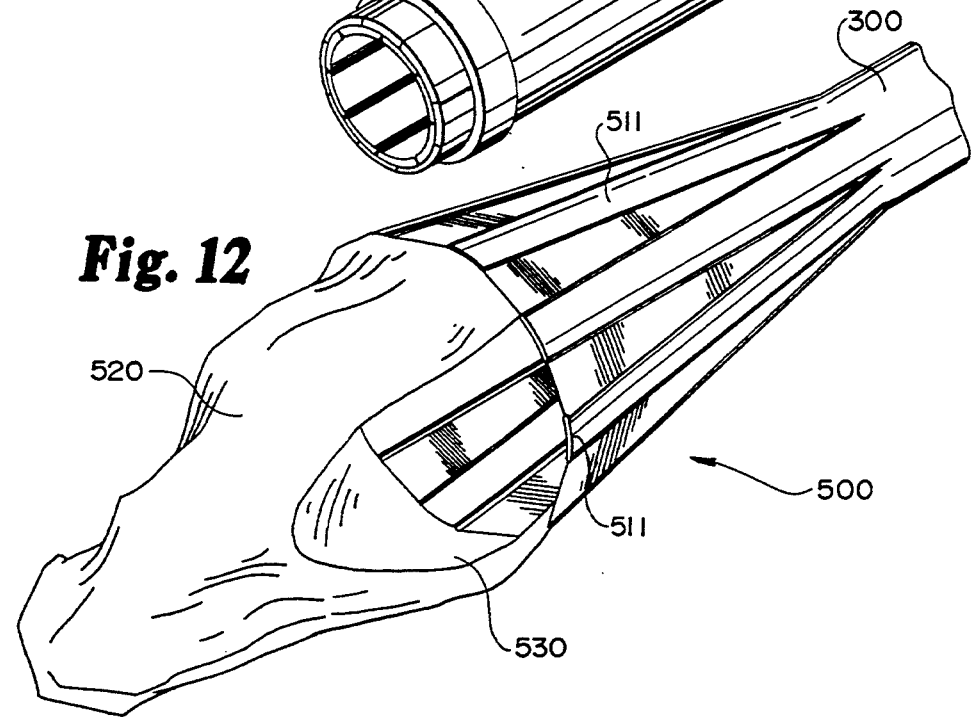
FIG. 12 is a fragmentary perspective view of a portion of the enveloping means of a second embodiment of the tissue and organ extractor of this invention showing a flexible membrane connected to the end of the enveloping means.

A second embodiment of the present invention is shown in FIGS. 10–12. This second embodiment differs from the first embodiment only in the construction and operation of the enveloping means. The other portions of this invention remain the same.

In the second embodiment, the enveloping means 500 comprises a flexible, outwardly flared rib portion 510 and a flexible, waterproof web material 520 attached thereto. The flexible, waterproof web material 520 has an opening mouth 530 located therein so that tissue or organs can enter the rib portion 510.

The rib portion 510 is biased outwardly by the ribs 511 formed at the end of the shank 300. The ribs 511 are integral with the shank 300, being formed by portions of the shank between parallel, longitudinal cuts. As in the first embodiment, the shank 300 and the ribs 511 may be formed of appropriate metals, metal-alloys, plastics or vinyls. In both of the embodiments of the present invention, the enveloping means (50 or 500) is approximately 7 to 13 centimeters in length. Consequently, the angle at which the ribs 511 or wires 39 flare outwardly relative to the end of the shank (30 or 300) will range between 10 and 30 degrees, approximately 10°–15° being preferred. Thus, in an enveloping means having a shank end opening diameter of approximately 10 mm, the opposite end, when fully flared open, will be approximately 2.5–3 cm in diameter. In the second embodiment of the present invention, the opening mouth 530 is approximately 2.5–4 cm in diameter.

The web material 520 is preferably made from any flexible yet sturdy, generally waterproof or liquid resistant, stain resistant fabric-like material such as suitable nylons, including rip-stop nylon, plastics or vinyls, including polypropylene meshes, or treated sail cloth. The selected web material 520 may be attached to the ribs 511 adjacent to the free end thereof in suitable ways, including sewn, heat-treated or welded, or otherwise mechanically joined. If a suitable material is chosen, e.g., an appropriate plastic, it is possible that the shank (30 or 300), wires and ribs (39 and 511, respectively), and web material (52 or 520) may be formed entirely of the selected material as a single, unitary piece of varying thickness.

Prior to insertion of the tissue and organ extractor into the cannula 4, a ring 540 is moved down over the rib portion 510 to collapse the rib portion 510. In this collapsed configuration, the rib portion 510 can fit through the cannula 4 to the interior of the abdominal cavity. Since the web material 520 is preferably formed from a flexible liquid proof fabric, it can collapse and easily fit through the cannula 4 with the rib portion 510.

As the tissue and organ extractor begins to travel through the cannula 4, the ring 540 engages either the top of the cannula 4 or a shoulder portion located in cannula 4. As discussed in connection with the first embodiment of this invention, the tissue and organ extractor will continue to travel through the cannula 4 resulting in the ring 540 traveling upwardly past the ribs 511. This allows the rib portion 510 to bias outwardly once it exits the cannula 4. An enlarged open area 530 is thus presented to the surgeon in the web material 520 and rib portion 510 to facilitate the insertion of a tissue or organ into the enveloping means 500.

Once the enveloping means 500 is positioned so that the opening 530 is in close proximity to the tissue or organ to be removed from a patient, a forceps can be inserted through the tissue and organ extractor. The forceps is then manipulated by the surgeon so that the forceps extends through the opening 530 and can grasp the tissue or organ and pull it through the opening 530 into the web material 520, as depicted. Of course, the tissue or organ could also be pulled further into the rib portion 510. After this is accomplished, the forceps is locked in place in relationship to the tissue and organ extractor by means of the locking lever described in conjunction with the first embodiment. The forceps, the tissue and organ extractor and cannula can then all be simultaneously removed from the abdominal cavity through the small puncture orifice.

As the tissue and organ extractor is removed through the puncture orifice, the web material 520 and rib portion 510 collapse and compress the tissue or organ located therein, generally elongating it so it may be extracted easily through the cannula or puncture wound. Thus, the extractor facilitates the removal of the tissue or organ from the body. Further, the enveloping means 500 as a whole provides a substantially sealed, leak-proof container that prevents the tissue or organ or parts thereof from breaking off and remaining in the abdominal cavity, as well as minimizes the escape of liquids associated with the tissue or organ into the abdominal cavity as the tissue or organ is extracted.

A third embodiment of the tissue and organ extractor 600 of the present invention is depicted in FIGS. 13–23. Referring to FIGS. 13 and 17, this embodiment of the extractor 600 comprises a handle 602, a handle shank 604, a plunger push rod 606 and a generally cone-shaped enveloping means 608. The extractor 600 also includes an extractor introducing shroud 610.

Referring to FIGS. 22 and 23, the handle 602 is generally cylindrical with a plurality of grip slots 612 evenly spaced about the outer surface thereof. A tissue clamp clearance hole 614 is axially centered in and extends through the handle 602. The handle 602 includes a base portion 616 and a distal portion 618. The distal portion 618 is movable relative to the base portion 616, and provides a chuck-type instrument locking means 620 including a collet 622 with a constriction surface 624. The constriction surface is manipulated by a constriction cam 626 driven by a collet chuck 628. The chuck 628 follows the collet draw cam 630 by means of a rider or follower pin 632. A constriction slot 634 is provided in the collet 622.

The handle 602 and handle shank 604 are removably connected to the plunger rod 606 at a bayonet connection 636, as shown in FIG. 17. Referring to FIGS. 18 and 19, one end of the handle shank 604 has a head 638 and carries a pair of substantially identical receiving channels 640 diametrically opposed to each other. At the end of each pin channel 640, the head 638 includes a pin stop area 642. As shown in FIG. 19, the pin channels 640 are designed to receive bayonet pins 644 carried by the plunger rod 606. The end of the plunger rod 606 also carries a coil spring 646 sandwiched between a plunger shoulder 648 and a floating washer 650.

The self-deploying, cone-shaped enveloping means 608 of the extractor 600 is formed by a pair of enveloping means leaves 652. As shown in FIGS. 14–16, before being connected to the extractor 600, the leaves 652 are generally thin, flat and triangularly shaped. The leaves 652 may be formed of a thin continuous piece of stainless steel, although other metallic foils, metallic alloys or plastics may be used. At its apex 654, each leaf 652 carries a pair of retainer holes 656. Opposite the apex 654, a plurality of cutout or stamped finger tabs 658 are provided to form a organ restraint bead 660. At one of the generally opposed side edges, extending between the apex 654 and the bead 660, leading edge 662 is provided by doubling a portion of the leaf back on itself and, at the other side edge, a plurality of inline organ retaining tabs 664 are formed. The tabs 664 are cut or stamped in the individual leaves 652 and deflected from the plane of the leaves as shown in FIG. 16.

The leaves 652 forming the cone shaped enveloping means 608 are connected to the plunger rod 606 as shown in FIGS. 13, 20 and 21. Specifically, at the end of the rod 606 opposite the end carrying the bayonet pins 644 (see FIG. 19), the plunger rod 606 carries a pair of diametrically opposed leaf retainer pins 670. Each pin 670 includes a pin shank 672 and a pin head 674, and may be pressfit into the body of the plunger rod 606. A reinforcement ring 678, with an elongated portion 676 to facilitate attaching the ring 678 to the leaves 652, is received about the pins 670.

The leaves 652 of the enveloping means 608 are permanently carried at the ends of the plunger 606 as depicted in FIG. 13 and 21. Specifically, the leaves 652 are curled or rolled into a generally circular configuration with the leading edge 662 of one leaf 652 generally adjacent to the barb carrying edge of the other leaf 652. The aligned retainer pin holes 656 are aligned with the borings in the plunger 606 for receiving the retainer pins 670. Pins 670 are inserted into the pinholes 656 of both leaves 652, then into the borings in the plunger 606. The reinforcing ring 678 around each pin shank 672 under the pin head 674 helps hold the leaves 652 in place. Because each leaf 652 is pinned into the inside of the generally cylindrical axial body of the plunger 606 at two spaced locations, they resiliently retain their curled shape. The beads 660 are formed by the spaced finger tabs 658 to allow the leaves curl.

To prepare the extractor for sale or use, the free end of the plunger rod 606, with the enveloping means 608 attached thereto, is inserted into the free open end of the shroud 610 and pushed into it while rotating in a clockwise direction until the spring carrying end of the plunger rod 606 extends past the shroud gib 611. Thus, the enveloping means 608 is moved into and carried in the shroud, the leaves 652 sliding against each other and being automatically compressed or wound into an overlaid, multi-layered cylindrical shape inside the shroud 610. Then, the plunger rod 606 carrying the enveloping means 608, surrounded by the shroud 610, is connected to the handle shank 604 by inserting the head 638 of the handle shank into the end of the rod 606 and pushing inwardly against the tension provided by the spring 646 until the bayonet pins 644 travel inwardly as far as possible into the pin channels 640, giving a quarter turn to the handle shank 604 and releasing it so that the spring 646 biases the bayonet pins 644 against the pin stops 642.

The extractor 600 of the third embodiment may be sold as a complete disposable unit assembled as outlined in the preceding paragraph. The extractor 600 also may be sold without the shroud 610, or the enveloping means 608 (mounted on the rod 606) may be sold as a unit for a single use, then disposal.

To use the extractor 600, the shroud 610, in place around the enveloping means 608, as depicted in FIG. 17, may be inserted into a typical cannula. To deploy the enveloping means 608, the extractor 600 is pushed inwardly (relative to the shroud 610, cannula and abdomen) while rotating in a clockwise direction. The resiliency of the leaves 652 causes the enveloping means 608 to self-deploy automatically as the leaves 652 are extended from the end of the introducer shroud 610. When fully deployed (as depicted in FIG. 13), the surgeon may insert a grasping instrument through the hollow passage running the length of the extractor 600, past the open end of the enveloping means 608, and draw the tissue to be removed inside the deployed cone-shaped enveloping means 608. The grasping instrument may be locked in place relative to the extractor 600 with the tissue inside the enveloping means 608 by rotating the upper half 618 of the handle 602 a quarter turn in a clockwise direction. The extractor 600 carrying the grasping instrument and the tissue inside the enveloping means 608 may be then withdrawn through the cannula, or the extractor 600 and cannula can be removed simultaneously from the patient's abdomen.

The third embodiment of the extractor 600 may be used with a flexible, substantially liquid-proof fluid containment web material 682 (similar to web material 520) attached thereto, as shown in FIGS. 24 and 25. FIG. 24 is intended to diagram representationally that the containment web takes the form of a "baggie" and to depict the position of the containment web 682 with respect to the extractor 600 generally, and more specifically, to the enveloping means 608 and plunger rod 606. Referring to FIG. 25, the web 682 is attached to the rod 606 between the spring carrying end thereof and the leaf retaining pins 670. A bushing 684 is connected to the rod 606. The bushing 684 has a slot 686 in the end adjacent to the spring carrying end of the rod 606. The web 682 is pulled through the bushing 686, laid over the slot 686, and a retaining ring 688 is pushed into the slot 686 capturing the web 682 between the slot 686 and ring 688. The large, free open end of the web 682 carries a draw string 690 which may be tightened to dose the end after a tissue is inside.

The preferred thickness of the leaves 652 is 0.002 inch, although a range of 0.001–0.003 inch may be used. The leaf retaining pins 670 may be welded to the plunger 606. Only a single row of tissue retaining barbs or teeth 664 is depicted, but more than one row may be used and the shape can be changed as long as they do not interfere with the collapse or expansion of the leaves 652. The instrument lock 620 is broadly a cam operated compressible surface that narrows the inside diameter of the passageway extending the length of the extractor 600.

Having thus described the invention, it is to be understood that the scope of the invention is limited only by the following claims.

I claim:

1. A tissue and organ extractor for use in laparoscopy along with auxiliary surgical instruments, said extractor for tissues, organs or the like from a body cavity during a laparoscopic surgical procedure and comprising:

a generally tubular, elongated rod-shaped shank having a handle end and a working end separable from said handle end, said shank having a longitudinal bore extending the length of said shank, said bore for receiving, said auxiliary instruments;

handle means for holding said extractor, said handle means at said handle end;

a flexible collapsible encompassing means having a first generally conical shape, a second generally cylindrical shape and an open end, said encompassing means for encompassing and compressing said tissue, organ or the like during the extraction thereof from said body cavity, being movable between said generally conical and cylindrical shapes and comprising two curled leaves, each said leaf having an apex connected to said working end, a free edge opposite said apex, said free edges substantially defining said open end, diverging side edges extending between said apex and said free edge and a body extending substantially continuously between said apex, said free edge and said side edges, one said side edge of each leaf being inside said encompassing means and the other side edge of each leaf being outside said encompassing means, whereby a compressive force exerted radially inwardly about said curled leaves tends to collapse said encompassing means from said generally conical shape into said generally cylindrical shape; and generally tubular shroud means for removably receiving said encompassing means and for applying said compressive force to said leaves.

2. The tissue and organ extractor according to claim 1, said encompassing means including retaining means for retaining said tissues, organs or the like.

3. The tissue and organ extractor according to claim 2, said retaining means comprising a raised area associated with at least one of said leaves, said raised area extending from said at least one leaf inside said body.

4. The tissue and organ extractor according to claim 1 further comprising containment means for substantially completely containing said tissues, organs or the like.

5. The tissue and organ extractor according to claim 4 including locking means for engaging and securing one of said auxiliary surgical instruments in fixed relationship to said extractor in said bore.

6. A surgical instrument for use in laparoscopy along with other auxiliary surgical instruments, said surgical instrument comprising:

a generally tubular, elongated rod-shaped shank having a handle end and a working end separable from said handle end, said shank having a longitudinal bore extending the length of said shank, said bore for receiving said auxiliary instruments;

handle means for holding said surgical instrument, said handle means adjacent to said handle end; and a collapsible encompassing means for encompassing and compressing a tissue, organ or the like, said encompassing means having a first truncated cone shape and a second generally cylindrical shape and comprising leaf means for collapsing and expanding, said leaf means having an apex, being coupled to said working end adjacent to said apex, and having a free edge opposite said apex, whereby a compressive force exerted radially inwardly about said encompassing means tends to collapse said encompassing means from said first truncated cone shape into said second generally cylindrical shape.

7. The surgical instrument according to claim 6, said leaf means having side edges extending between said apex and said free edge and a body extending substantially continuously between said apex, said free edge and said side edges.

8. The surgical instrument according to claim 7, said side edges diverging from said apex, and said leaf means being curled, one of said side edges being inside said body and the other of said side edges being outside said body.

9. The surgical instrument according to claim 8, said encompassing means including retaining means for retaining said tissue, organ or the like.

10. The surgical instrument according to claim 6 and generally annular application means for applying said compressive force, said application means slidable, concentric and removable with respect to said encompassing means.

11. A tissue and organ extractor comprising:
a hollow member having a first end and a second end;
a plurality of outwardly biased ribs connected to said first end of said hollow member defining a rib portion having a normally outwardly extending configuration;

a plurality of flexible material connected between said plurality of outwardly biased ribs so that said plurality of outwardly biased ribs and said plurality of flexible material define an interior portion of said tissue and organ extractor; and a flexible, waterproof material connected to said plurality of outwardly biased ribs and to said plurality of flexible material, said flexible, waterproof material defining an opening therein to allow access to said interior portion of said tissue and organ extractor.

12. The tissue and organ extractor of claim 11 further comprising a locking means adjacent to said second end of said hollow member for fixedly positioning a second instrument with respect to said tissue and organ extractor.

13. The tissue and organ extractor of either of claims 11 or 12 further comprising a means for collapsing said outwardly biased ribs so that said rib portion does not have an outwardly extending configuration.

14. A tissue and organ extractor comprising:
a hollow member having a first end and a second end, said first end defining a flexible portion having a normally outwardly extending frustoconical configuration; and a flexible material resistant to the passage of liquid connected to said first end of said hollow member, said flexible material defining an opening therein allowing access to the interior of said flexible material, wherein said flexible portion is defined by a plurality of ribs formed integrally with said hollow member and by said flexible material connecting said plurality of ribs.

15. The tissue and organ extractor of claim 14 further comprising a means for collapsing said flexible portion into a generally tubular configuration.

16. The tissue and organ extractor of claim 15 further comprising a locking means adjacent to said second end of said hollow member for fixedly positioning a second instrument with respect to said tissue and organ extractor.

17. The tissue and organ extractor of claim 14 further comprising a locking means adjacent to said second end of said hollow member for fixedly positioning a second instrument with respect to said tissue and organ extractor.

18. An extractor for use in endoscopy comprising:
a generally tubular, elongated shank having a working end, a second end and a longitudinal bore; and at least one leaf having an apex connected to said working end and a free edge opposite said apex, said at least one leaf having a generally cone-shaped uncollapsed shape and a generally cylindrical collapsed shape.

19. The extractor according to claim 18, said at least one leaf having side edges extending between said apex and said free edge and a leaf body extending substantially continuously between said apex, said free edge and said side edges.

20. The extractor according to claim 19, said side edges diverging from said apex, and said at least one leaf being curled, one of said side edges being inside said leaf body and the other of said side edges being outside said leaf body.

21. The extractor according to claim 20 and retaining means for retaining an object to be extracted within said leaf body.

22. The extractor according to claim 21, including containment means for substantially completely containing an object to be extracted.

23. The extractor according to claim 21, said retaining means comprising a plurality of raised portions on an inside surface of said leaf body.

24. The extractor according to claim 22, said containment means comprising a flexible material resistant to the passage of liquid operably coupled to said at least one leaf and defining an opening for receiving said object.

25. The tissue and organ extractor according to claim 18 including locking means for engaging and securing an auxiliary surgical instrument in fixed relationship to said extractor in said bore.

26. The extractor according to claim 18 and means for moving said at least one leaf between said uncollapsed and collapsed shapes.

27. The extractor according to claim 26, said means for moving comprising a generally cylindrical tubular member generally concentrically and slidably positioned with respect to said shank.

* * * * *

UNITED STATES PATENT AND TRADEMARK OFFICE
CERTIFICATE OF CORRECTION

PATENT NO. : 5,370,647
DATED : December 6, 1994
INVENTOR(S) : Graber, John et al.

It is certified that error appears in the above-indentified patent and that said Letters Patent is hereby corrected as shown below:

In column 2, line 37, delete "damp" and insert --clamp--

In column 2, line 54, delete "dose" and insert --close--

In column 6, line 35, delete "dose" and insert --close--

In column 10, line 27, delete "dose" and insert --close--

Signed and Sealed this

Second Day of July, 1996

Attest:

BRUCE LEHMAN

Attesting Officer

Commissioner of Patents and Trademarks